United States Patent [19]

Lipton

[11] Patent Number: 4,742,827
[45] Date of Patent: May 10, 1988

[54] HEATING PAD

[76] Inventor: Barry Lipton, 11433 Flints Grove La., Gaithersburg, Md. 20878

[21] Appl. No.: 909,332

[22] Filed: Sep. 19, 1986

[51] Int. Cl.⁴ .............................................. A61F 7/00
[52] U.S. Cl. ................................... 128/380; 128/384; 128/402; 128/403
[58] Field of Search ............... 128/379, 380, 384, 385, 128/399, 402, 403

[56] References Cited

U.S. PATENT DOCUMENTS

| | | | |
|---|---|---|---|
| 551,939 | 12/1895 | Weber | 128/403 |
| 723,797 | 3/1903 | Williams | 128/379 |
| 1,594,053 | 7/1926 | Evans | 128/379 |
| 2,071,706 | 2/1937 | Reach | 128/380 |
| 2,429,583 | 10/1947 | Ogle | 128/380 |
| 3,889,684 | 6/1975 | Lebold | 128/403 |
| 4,061,897 | 12/1977 | Thykeson | 128/379 |
| 4,512,830 | 4/1985 | Hulett et al. | 128/380 |

Primary Examiner—Carl D. Friedman
Assistant Examiner—Michael Safavi
Attorney, Agent, or Firm—Oblon, Fisher, Spivak, McClelland & Maier

[57] ABSTRACT

A heating pad includes a pad member formed of soft and flexible material, including a flat and substantially rectangular central portion defining ends spaced in the direction of elongation of the central portion and sides spaced in a direction transverse to the direction of elongation. A substantially semicircular cut-out is provided in the central portion, the cut-out extending from an intermediate portion of one of the sides towards the other of the sides. A flat substantially rectangular extending portion projects from one side adjacent each of the ends in a direction substantially transverse to the direction of elongation of the central portion. Straps or other such means are provided for selectively connecting the opposite ends while a heating element may be positioned within the pad.

10 Claims, 5 Drawing Sheets 4,742,827

HEATING PAD

BACKGROUND OF THE INVENTION

1. Field of the Invention:

The present invention relates to a heating pad, and more particularly to a heating pad for providing bilateral moist heat for treatment of three related muscle groups.

2. Description of the Related Art:

It is well known that heat, and in particular moist heat, can be used in the therapeutic treatment of injured muscles. It has also been known that muscle injuries often occur simultaneously in muscles which comprises a group for performing a given task. For example, the Temporalis (Temporoparietalis and Auriculares), together with the Masseter, Pterygoid and Hyoid muscles operate as a group in mastication and are sometimes injured as a result of trauma in automobile accidents. Effective therapeutic heat treatment of these muscles requires that bilateral heat treatment of all the muscles of this group be performed simultaneously.

Similarly, the muscles of the upper back, rear shoulder and neck form a group used in flexure of these areas of the body and may be injured during "whiplash". These muscles, i.e., the Mylohyoids, upper Trapezius, Sternocleidomastoid and the Insertion of the Internal Pterogoid, should also receive bilateral simultaneous therapeutic moist heat treatment.

Yet another group of muscles requiring simultaneous bilateral heat treatment is used in the flexure of the neck and chest, and include the upper cervical, the upper ends of the Trapezius, the lower portion of the Sternocleidomastoids and the upper Pectoralis. This third group is also sometimes injured during "whiplash" in a vehicle accident.

Moist heat treatment pads shaped for specific parts of the body are well known. An example is the "Hydrothero Pad" manufactured by Roberts Manufacturing Company of Baltimore, Md. For the treatment of the above groups of muscles, Roberts manufactures an essentially retangular pad. However, the rectangular pad is incapable of adequately covering any individual muscle group, or of simultaneously moist heat treating all of the muscles of each of the above groups without uncomfortable binding or "cuffing" of the pad against areas to be treated.

SUMMARY OF THE INVENTION

It is an object of the present invention to provide a heating pad capable of being comfortably and safely positioned in at least three positions wherein all of the muscles of each of the above groups is simultaneously and evenly heat treated.

According to the invention, the heating pad includes a flexible pad member formed of a soft flexible material and including a flat, substantially rectangular central portion defining ends spaced in the direction of the elongation of the central portion, and sides spaced in a direction transverse to the direction of elongation. An arcuate cut-out is provided in the central portion, the cut-out extending from an intermediate portion of one of the sides towards the other of the sides. A flat and substantially rectangular extending portion extends from the one side adjacent each of the ends of the pad and in a direction substantially transverse to the direction of elongation of the central portion. Means, such as straps, are provided for selectively and securely connecting the opposite ends. Means, such as a heat retentive mass or electric heating coils, are provided in the pad for heating the same. The heating means are shaped so as to be able to evenly heat the entirety of the pad member.

The so shaped heating pad is sized so as to be able to simultaneously heat treat all muscles of the first, (mastication) group when in a first position, all muscles of the second (neck and back) group when in a second position and all muscles of the third (neck and chest) group when in a third position.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
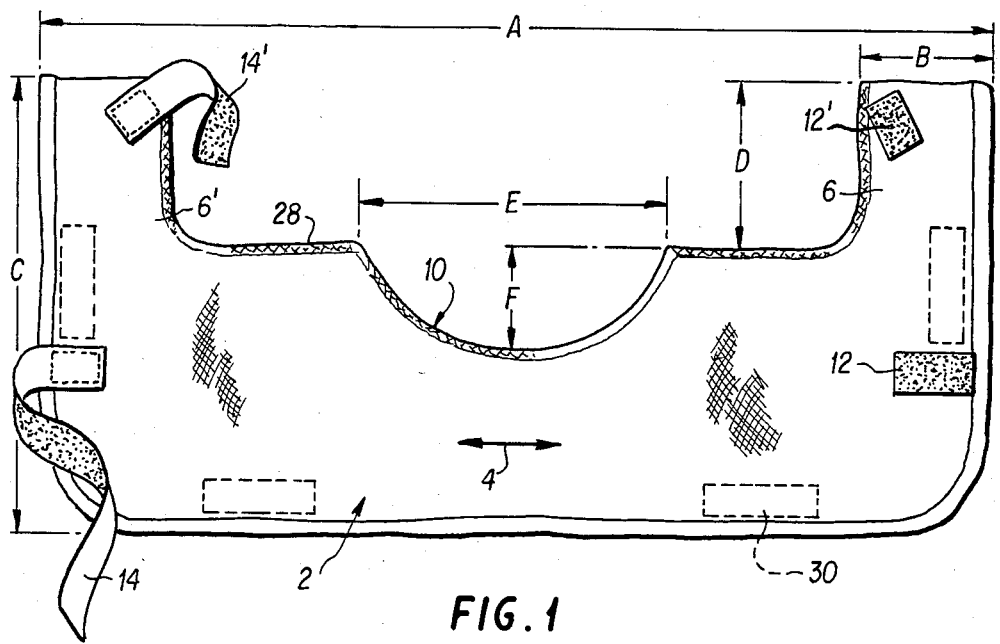
FIG. 1 is a plan view of a first embodiment of the heating pad of the invention.

The heating pad of the invention will now be described with reference to the accompanying Figures, wherein the same or corresponding reference numerals are used to identify the same or corresponding parts throughout the several views.

The general shape of a first embodiment of the invention is shown in plan in FIG. 1. It includes an elongate rectangular central portion 2 having a direction of elongation shown by arrows 4, and a pair of substantially rectangular extending portions 6 and 6' which extend from the ends of the central portion in a direction transverse to the direction of elongation. The side of the central portion between the extending portions 6 and 6' is provided with a generally semi-circular shaped cutout 10. Velcro pads 12 and 12' are attached to one end of the central portion and to the extending portion 6, while straps 14 and 14' having Velcro (trademark for hook and loop type fabric connector) thereon are respectively fixed to the opposite end of the central portion and to the extending portion 6'.

The straps 14 and 14' comprise means for selectively connecting the opposite ends of the central portion to one another and to the extending portions.

Figure 2:
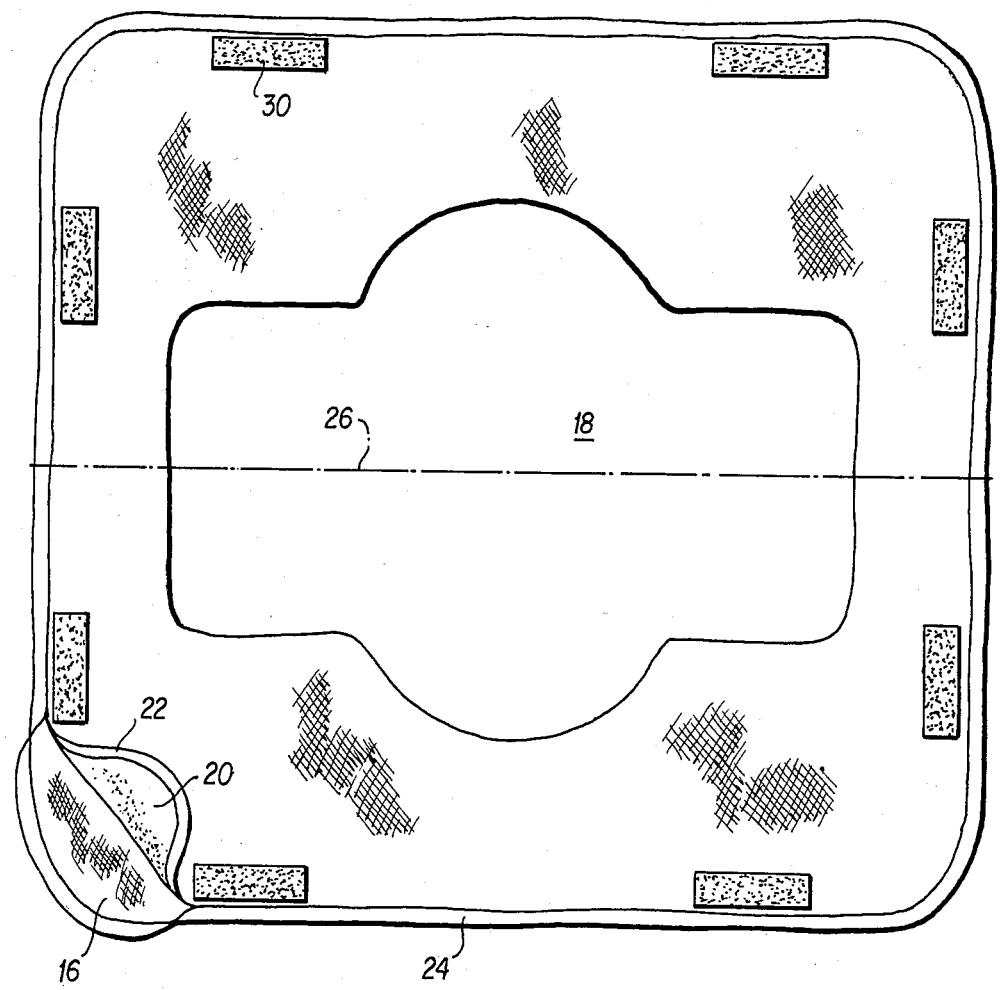
FIG. 2 shows the first embodiment in an intermediate state of manufacture.

The pad of FIG. 1 is made by folding a laminated pad preform having the shape shown in FIG. 2. In FIG. 2, a first layer 16 of soft cloth, such as terrycloth, has a substantially square or rectangular shape and is provided with a central opening 18. An intermediate layer 20 of soft absorbent material, such as lamb's wool, is laid on the bottom layer 16. An upper layer 22, which may also be formed of terrycloth, is then laid on the laminate of the bottom layer 16 and the intermediate layer 20. The outer peripheral edges of the layers 16, 20 and 22 are then sewn together, optionally with the use of reinforcement strip 24.

The opening 18 may be formed in each of the layers prior to assembly of the laminate, or may be cut in the assembled laminate. Similarly, the exterior periphery of the layers of the laminate may be cut prior to assembly, or the laminate may be assembled and then cut for final sizing.

The pad preform is then folded along line 26 to result in the pad having the shape shown in FIG. 1. The two halves of the folded pad preform are sewn about the entire periphery of the opening 18 to form a sewn seam 28 in the folded pad. The two halves of the resulting pad are held together about the remainder of their periphery by Velcro strips 30, as a result of which the halves of the pad can be separated at the strips 30 for the insertion of a heat retentive mass. The Velcro strips can then be resealed so as to retain the heat retentive mass.

The heat retentive mass, which is not shown, may be conventional, except in shape. For example, it can be in the form of a textile bag filled with wet heated sand. The bag should be shaped so that it is capable of providing heat to the entirety of the pad, including the rectangular extending portions 6 and 6'. For example, the bag containing the heat retentive material can also have the shape of an elongate rectangle having rectangular extending portions and a cut-out, as shown in FIG. 1.

Figure 3:
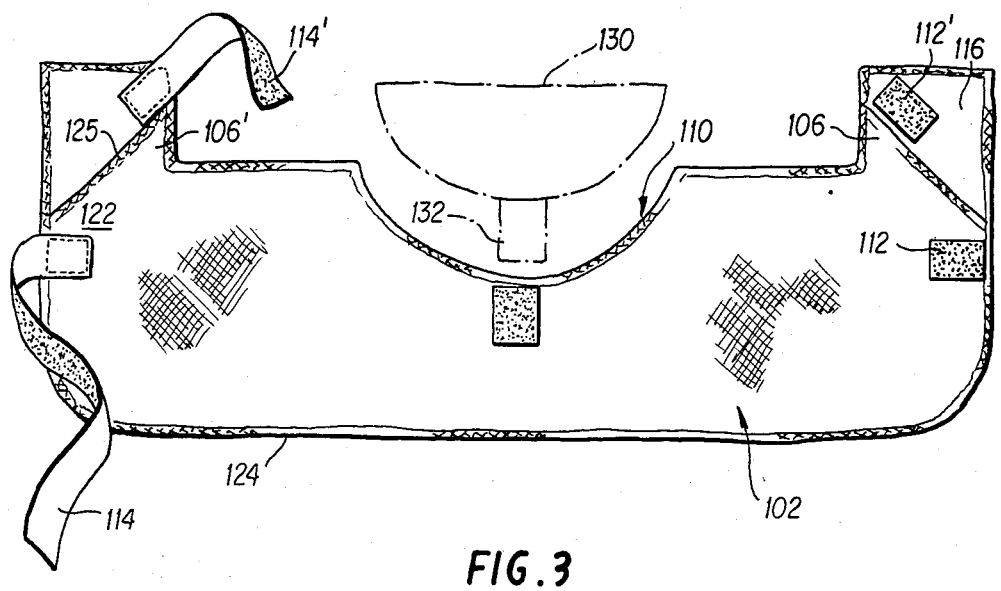
FIG. 3 is a plan view of a second embodiment of the heating pad of the invention.

The second embodiment of FIG. 3 includes an elongate central portion 102, rectangular extending portions 106 and 106', and a cut-out 110, and has an overall shape similar to that of the first embodiment. The second embodiment is used with an electrical heating element. It is formed of two layers of lambs wool sewn along their periphery by stitches 124. The bottom layer 116 has fully extending rectangular extending portions, while the rectangular extending portions of the upper layer 122 terminate at edge 125 which is not sewn to the lower layer 116. As a result, an electrical heating element can be inserted between the layers 116 and 122 by insertion at the edge 125. The electrical heating element is preferably flexible and may be curved so as to extend at least partly in to the extending portions 106 and 106'. Velcro pads 112 and 112' cooperate with Velcro covered straps 114 and 114' for securement of the ends of the pad to one another during use.

Shown in dashed lines in FIG. 3 and provided with reference numeral 130 is an optional neck flap which may be connected to the cut-out 110 by strap 132.

Figure 4:
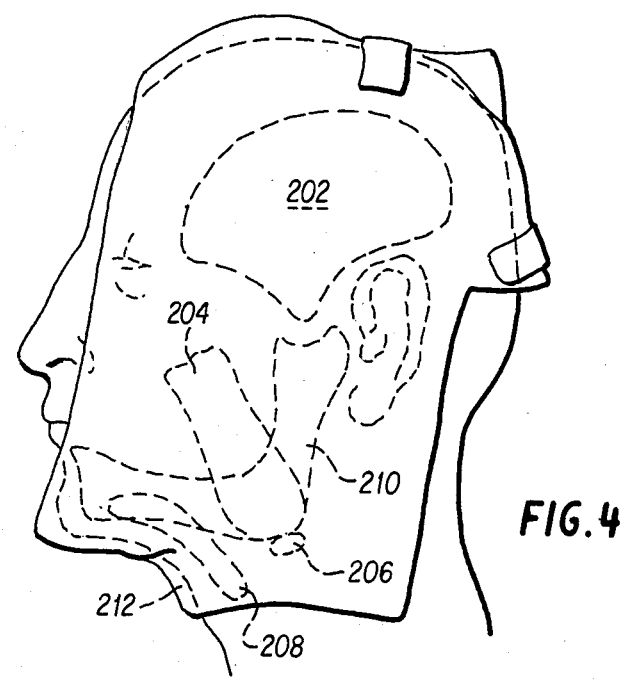
FIG. 4 shows the heating pad of the invention applied to the mastication group muscles.

The use of the heating pad according to the invention will now be described:

FIG. 4 shows the first or mastication muscle group with the pad of the invention superimposed thereon in dashed lines. As can be seen, the pad is applied with the cut-out 10 circling the front half of the neck, the portions of the central portion 2 on either side of the cut-out being draped upwardly on either side of the head and the rectangular extending portions 6 and 6' extending rearwardly toward one another at the upper back of the head. The straps 14 and 14' are attached to the corresponding velcro strips 12 and 12'. As can be seen, the Temporalis 202, Massiters 204, Insertion of the Internal Pterygoid 206 and Hyoid muscles 208 are all covered by the pad. Element 210 is the jawbone. The provision of the cut out 10 permits the pad to be positioned sufficiently posteriorly so that the extending portions 6 and 6' fully cover the Temporalis without the pad binding against the neck at 212 the Temporalis and hindering swallowing or breathing. The pad contains a moist heat retentive mass, and so applies wet therapeutic heat treatment to all of the first group of muscles.

Figure 5:
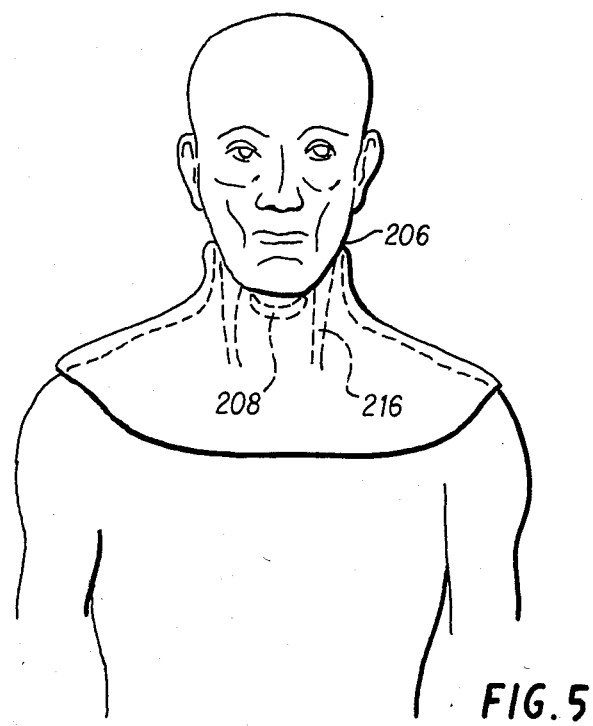
FIG. 5 is a posterior view of the heating pad of the invention applied to the back and neck group muscles.
Figure 6:
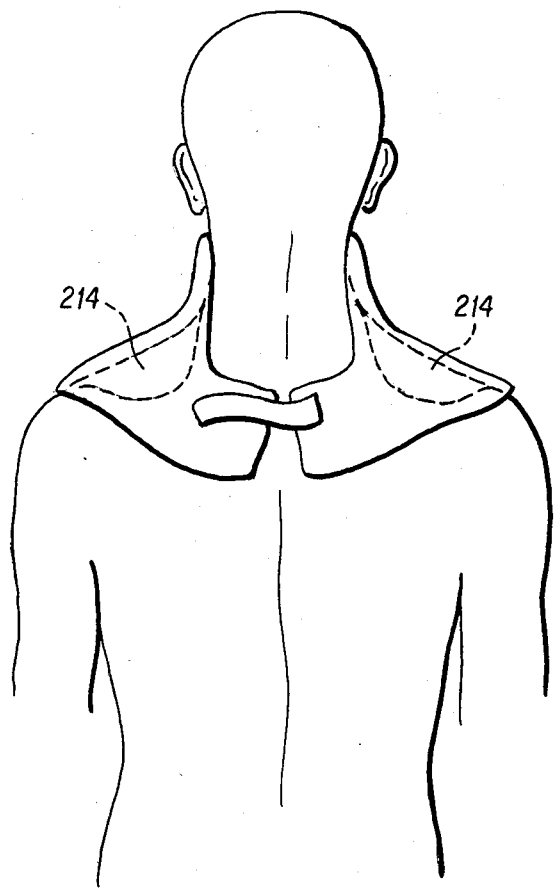
FIG. 6 is an anterior view of the pad in the position of FIG. 5.

For the application of therapeutic heat to the second group of back and neck muscles, the heating pad is positioned as shown in FIGS. 5 and 6. As can be seen from the Figures, the cut-out 10 permits extending portions 6 and 6' to drape around the back and cover the upper Trapezius 214 while at the same time the central portion 2 of the heating pad fits about the neck and comfortably covers the Sternocleidomastoid 216, the Insertion of the Internal Pterogoid and the Molyhyoids without tightly binding and without impeding respiration and swallowing. It may be appreciated that without the cut out 10 the central portion 2 would wither cuff at the neck and restrict breathing or the extending portions would not cover the upper Trapezius.

Figure 7:
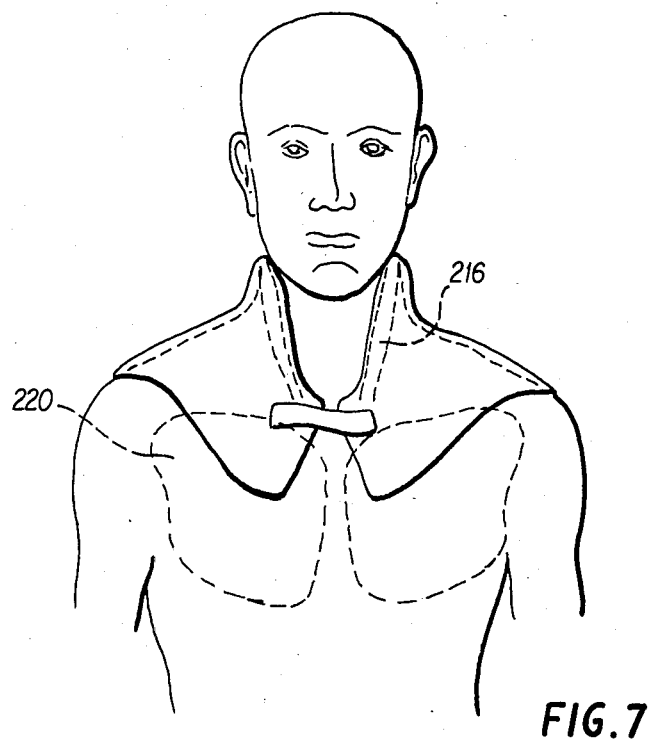
FIG. 7 is an anterior view of the heating pad of the invention applied to the neck and chest group muscles.
Figure 8:
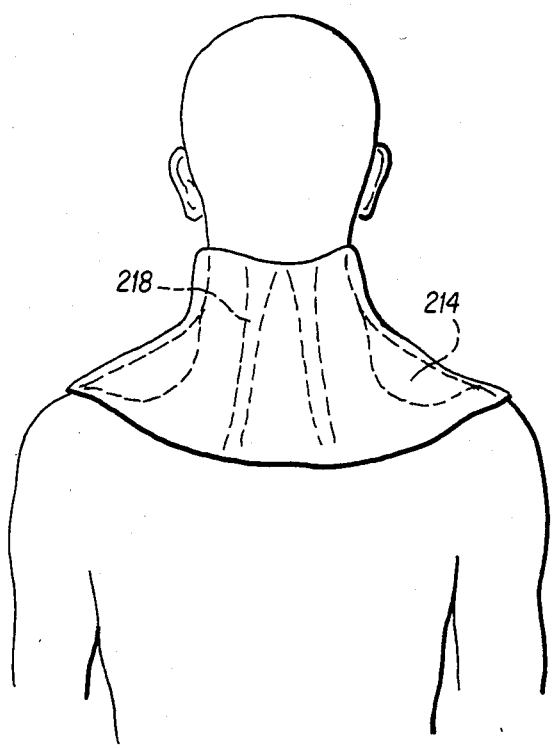
FIG. 8 is a posterior view of the pad in the position of FIG. 7.

The third position for applying therapeutic heat to the third group of muscles of the neck and chest is shown in FIGS. 7 and 8. As seen in FIG. 7, the additional length provided by the extending portions 6 and 6' permit them to drape over the chest to cover both the upper end of the Trapezius 214, the Cervical 218 and the upper Pectoralis 220. The cut-out 10 again permits the heating pad to comfortably conform to the neck such that the Sternocleidomastoid is covered.

Accordingly, it may be appreciated that all three muscle groups may be heat treated by a single heating pad due to the unique shape thereof including features which accommodate the body configurations in a novel and unexpected manner, these features including the flat and substantially rectangular central portion having a substantially semi-circular cut-out, together with the rectangular extending portions extending from the ends of the rectangular portion.

Preferred, but not limiting, dimensions of the pad are:

| | |
|---|---|
| A - 23 in. | D - 4 in. |
| B - 3.5 in. | E - 6 in. |
| C - 10.5 in. | F - 2.5 in. |

Obviously, numerous modifications and variations of the present invention are possible in light of the above teachings. It is therefore to be understood that within the scope of the appended claims, the invention may be practiced otherwise than as specifically described herein.

What is claimed as new, and desired to be secured by Letters Patent of the United States is:

1. A heating pad comprising:
   a pad member formed of soft flexible material and including:
   (a) a flat, substantially rectangular central portion defining two elongate substantially parallel sides extending along a direction of elongation and two ends shorter than said elongate sides and spaced in the direction of elongation of said central portion, said elongate sides being spaced in a direction transverse to said direction of elongation,
   (b) an arcuate cut-out in said central portion, said cut out extending from an intermediate portion of one of said sides towards the other of said sides, (c) a flat, substantially rectangular extending portion projecting from said one of said sides adjacent each of said ends and in said direction substantially transverse to said direction of elongation of said central portion;

means for selectively connecting opposite ones of said ends; and means for heating the entirety of said central portion of said pad member.

2. The heating pad of claim 1 wherein each of said extending portions has an edge defining an extension of one of said ends of said central portion and extending away from said other of said sides of said central portion.

3. The heating pad of claim 1 wherein said means for heating are positioned within said pad member.

4. The heating pad of claim 3 wherein said means for heating comprises a heat retentive mass having a shape corresponding to a shape of said pad member.

5. The heating pad of claim 3 wherein said means for heating comprise at least one electric heating element sized and shaped as to be able to heat said pad member.

6. The heating pad of claim 3 wherein said pad member includes at least two layers, including means for permitting insertion of said heating means between said layers.

7. The heating pad of claim 1 including means for selectively connecting each of said opposite ends to said extending portion projecting from the other of said opposite ends.

8. The heating pad of claim 7 wherein said means for selectively connecting said opposite ends comprise straps fixed to at least one of said ends.

9. The heating pad of claim 5 including a removable neck flap attached to said central portion adjacent said cut-out.

10. The heating pad of claim 1 wherein said pad member is sized and shaped to comprise means for simultaneously heat treating all muscles of a first mastication group when in a first position, all muscles of a second neck and back group when in a second position and all muscles of a third neck and chest group when in a third position, wherein:

(a) said first group comprise the Temporalis, Masseter, Insertion of the Internal Pterygoid and Hyoid muscles, bilaterally.

(b) said second group comprises the Mylohyoid, Sternocleidomastoid, Insertion of the Internal Pterygoid and upper Trapezius muscles, bilaterally, and (c) said third group comprises the upper Cervicle, Trapezius, Sternocleidomastoid and upper portions of the Pectoralis muscles, bilaterally.

* * * * *